(12) United States Patent
Marsh et al.

(10) Patent No.: US 8,940,675 B2
(45) Date of Patent: Jan. 27, 2015

(54) CLEANSING COMPOSITION AND A WET WIPE COMPRISING THE SAME

(71) Applicant: The Procter & Gamble Company, Cincinnati, OH (US)

(72) Inventors: Randall Glenn Marsh, Hamilton, OH (US); Jacqueline Marie Duderstadt, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/163,190

(22) Filed: Jan. 24, 2014

(65) Prior Publication Data

US 2014/0208531 A1    Jul. 31, 2014

Related U.S. Application Data

(60) Provisional application No. 61/758,802, filed on Jan. 31, 2013.

(51) Int. Cl.
| | |
|---|---|
| *C11D 3/22* | (2006.01) |
| *C11D 3/382* | (2006.01) |
| *A61K 8/73* | (2006.01) |
| *C11D 7/44* | (2006.01) |
| *A47L 13/17* | (2006.01) |
| *A61K 8/37* | (2006.01) |

(Continued)

(52) U.S. Cl.
CPC . *C11D 7/44* (2013.01); *A47L 13/17* (2013.01); *A61K 8/37* (2013.01); *A61K 8/73* (2013.01); *A61Q 19/00* (2013.01); *A61K 8/0208* (2013.01); *A61K 2800/48* (2013.01)

USPC .......... 510/151; 510/130; 510/157; 510/438; 510/470; 424/488; 424/496

(58) Field of Classification Search
USPC .......... 510/130, 151, 157, 438, 470; 424/488, 424/496
See application file for complete search history.

(56) References Cited

U.S. PATENT DOCUMENTS

| | | |
|---|---|---|
| 4,894,250 A | 1/1990 | Musson et al. |
| 6,831,107 B2 | 12/2004 | Dederen et al. |

(Continued)

FOREIGN PATENT DOCUMENTS

| | | | | |
|---|---|---|---|---|
| CN | 102138675 | * | 8/2011 | ............ A23L 1/326 |
| EP | 1676557 A2 | | 7/2006 | |
| WO | WO 2007/091016 A1 | | 8/2007 | |
| WO | WO 2008/007059 A1 | | 1/2008 | |

OTHER PUBLICATIONS

Material Safety Data Sheet, Nutricol ME 8731 Konjac Flour, MSDS Ref. No. 100575, Date Approved: Oct. 25, 2006, Revision No. 1, FMC BioPolymer.

(Continued)

*Primary Examiner* — Brian P Mruk
(74) *Attorney, Agent, or Firm* — Brian M. Bolam

(57) ABSTRACT

The present disclosure includes cleansing compositions for removing soils from surfaces. Tee cleansing composition may be loaded ones a substrate to form a wet wipe. The cleansing composition may include a glucomannan and a synergy enhancing agent. The synergy enhancing agent may include xanthan gum. The synergy enhancing component may include xanthan gum and carrageenan. The wet wipe may be used to assist in the removal of soils such as feces, menses, and urine from skin.

11 Claims, 2 Drawing Sheets

(51) Int. Cl.
*A61Q 19/00* (2006.01)
*A61K 8/02* (2006.01)

(56) References Cited

U.S. PATENT DOCUMENTS

| | | |
|---|---|---|
| 2002/0183216 A1 | 12/2002 | Koenig et al. |
| 2003/0232965 A1* | 12/2003 | Bergeron ............... 530/300 |
| 2007/0269519 A1 | 11/2007 | Georgiades et al. |
| 2008/0154225 A1 | 6/2008 | Phan |
| 2010/0255076 A1 | 10/2010 | Heber et al. |
| 2012/0121671 A1 | 5/2012 | Goldstein |
| 2013/0029933 A1 | 1/2013 | Schnitzler et al. |
| 2013/0287708 A1 | 10/2013 | Silberstein |

OTHER PUBLICATIONS

International Search Report, PCT/US2014/012983, mailed Apr. 14, 2014, 13 pages.

Williams, P.A., et al., "Investigation of the Gelation Mechanism in κ-Carrageenan/Konjac Mannan Mixtures Using Differential Scanning Calorimetry and Electron Spin Resonance Spectroscopy", Macromolecules, vol. 26, No. 20, Sep. 1, 1993, pp. 5441-5446, XP055112177.

Anonymous, "Glucomannan", Dec. 31, 2002, XP055112171, http://www.konjacfoods.com/gum.htm.

* cited by examiner

ND A WET
CLEANSING COMPOSITION AND A WET WIPE COMPRISING THE SAME

CROSS REFERENCE TO RELATED APPLICATIONS

This application claims the benefit of US provisional patent application 61/758,802 filed Jan. 31, 2013, the substance of which is hereby incorporated by reference.

FIELD OF THE INVENTION

The present disclosure includes a cleansing composition useful for removing soils from surfaces. The cleansing composition may be incorporated into a substrate to form a wet wipe for cleaning soils from surfaces.

BACKGROUND OF THE INVENTION

Wet wipes may be useful for cleaning hard and soft surfaces. Wet wipes may also be useful for delivering functional materials to a surface. For example, a wet wipe may provide skin benefits, such as conditioning and/or moisturizing the skin, or protection from or treatment of diaper rash. Wet wipes may comprise a substrate, generally a nonwoven material, and a cleansing composition. The cleansing composition may be aqueous, in which the components are freely soluble or stably dispersed within water. The cleansing composition may be suitable for use on a variety of surfaces, including, for example, skin, wood, or countertops. For wet wipes for use on skin, the cleansing composition may comprise surfactants, oil materials, skin care agents, pH buffers, solvents, preservatives, or other additives for cleaning and/or treating the skin.

Some wet wipes may include synthetic nonwoven materials. A wet wipe comprised partially or wholly of synthetic fibers, such as polypropylene, may have a higher surface area than a wet wipe comprised of a greater percent of natural fibers. In order to provide the same sensory or wetness perception as a wet wipe comprising natural fibers, a wet wipe comprising primarily synthetic fibers may have to be loaded with more cleansing composition. Without being bound by theory, it is believed that loading the wet wipe with more cleansing composition may reduce the adhesive interactions between the soil and the substrate. A relatively high cleansing composition load may cause a lubricating layer to form at the soil-substrate interface. Further, the presence of a relatively high cleansing composition load within the wipe may reduce the absorbent capacity of the wipe as more of the wipe structure is already filled with liquid. As a result, the soil may smear or spread over the surface rather than be removed from the surface by the wet wipe. As such, the cleaning performance of the wet wipe may be reduced at relatively high cleansing composition loads.

As a result, it would be beneficial to provide a synthetic wet wipe having a good sensory perception to consumers and a good cleaning performance.

SUMMARY OF THE INVENTION

Aspects of the present disclosure include a cleansing composition comprising a glucomannan, xanthan gum, and carrageenan. The glucomannan may comprise *Amorphophallus konjac* root powder. The cleansing composition may comprise less than about 0.25% by weight of the glucomannan. The cleansing composition may have a peak complex viscosity of between about 0.8 Pa·s to about 7.0 Pa·s. The ratio of xanthan gum to glucomannan to carrageenan may be from about 1:0.02:0.03 to about 1:0.33:0.5.

A wet wipe may comprise a substrate and the cleansing composition. The substrate may comprise a nonwoven. The wet wipe may comprise from about 200% to about 600% weight of the cleansing composition to weight of the substrate.

Aspects of the present disclosure include a wet wipe comprising a substrate and a cleansing composition. The cleansing composition may comprise a glucomannan and a synergy enhancing agent. The cleansing composition may comprise less than about 0.5% by weight of an oil material. The synergy enhancing agent may comprise xanthan gum. The synergy enhancing agent may comprise xanthan gum and carrageenan. The synergy enhancing agent may comprise locust bean gum. The synergy enhancing agent may comprise a starch. The synergy enhancing agent may comprise gellan gum. The synergy enhancing agent may comprise alginate. The cleansing composition may comprise less than about 0.25% by weight of the glucomannan. The cleansing composition may have a peak complex viscosity of between about 0.8 Pa·s to about 7.0 Pa·s.

Aspects of the present disclosure include a method of preparing a cleansing composition. The method comprises the steps of: combining a glucomannan, carrageenan, and water; dispersing the glucomannan and the carrageenan in the water; combining xanthan gum with the dispersion of glucomannan, carrageenan, and water; and mixing the xanthan gum in the dispersion of glucomannan, carrageenan, and water to form a cleansing composition. The cleansing composition may have a peak complex viscosity of between about 0.8 Pa·s to about 7.0 Pa·s. The ratio of xanthan gum to glucomannan to carrageenan may be from about 1:0.02:0.03 to about 1:0.33:0.5.

Aspects of the present disclosure include a cleansing composition comprising a glucomannan and carrageenan. The ratio of glucomannan to carrageenan is from about 0.02:0.03 to about 0.33:0.5.

DETAILED DESCRIPTION OF THE DRAWINGS

DETAILED DESCRIPTION OF THE INVENTION

Figure 1:
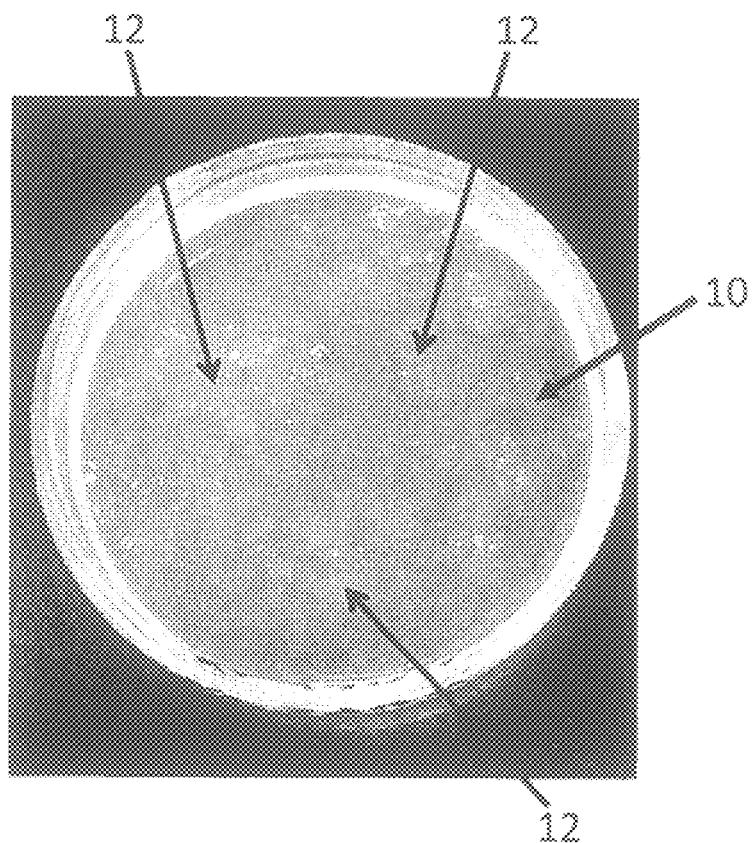
FIG. 1 is a black and white photograph of a beaker containing a non-homogeneous dispersion of a glucomannan in water.

The following definitions may be useful in understanding the present disclosure:

"Soil" refers herein to matter that is extraneous to a surface being cleaned. For example, soils include body exudates, household matter, and outdoor matter. Body exudates include feces, menses, urine, vomitus, mucus, and the like. Household matter includes food, beverages, combinations thereof, and the like. Outdoor matter includes dirt, mud, snow, paint, crayons, and the like.

"Substrate" refers herein to a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes.

"Adhesive interaction" refers herein to the degree of attraction between a soil and a substrate.

"Loading" refers to a process of applying a cleansing composition to a substrate to form a wet wipe. A "loaded" substrate is associated with a cleansing composition.

"Oil material" includes substances that are liquid at room temperature and insoluble in water.

"Q.S." refers herein to "quantum sufficit" and is a sufficient percentage of water added to the composition to bring the overall composition to 100%.

As used herein, percentages are given as the weight of the component to the total weight of the cleansing composition, unless otherwise indicated. Percentages reflect 100% active component material. For example, if a component is available in a dispersion at a concentration of 50% component to dispersion, by weight, twice as much of the dispersion, by weight, would be added to the cleansing composition to provide the equivalent of 100% active component.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

The ease with which soils are removed from a surface may be related to the strength of the adhesive interactions between the soil and the surface and between the soil and the wet wipe. Increasing the adhesive interaction between the soil and the wet wipe may enable more effective removal of the soil from the surface. More particularly, good cleaning performance of a wet wipe may occur when the adhesive interaction between the soil and the wet wipe is greater than the adhesive interaction between the soil and the surface. It has been found that wet wipes having a cleansing composition comprising a glucomannan have an increased adhesive interaction between the soil and the wet wipe compared to a wet wipe having a cleansing composition without a glucomannan. In addition, it has been found that cleansing compositions comprising glucomannans in combination with an additional compound, referred to herein as a "synergy enhancing agent," may further increase the adhesive interaction between a soil and a substrate. As a result, relatively low concentrations of a glucomannan may be used to achieve a strong adhesive interaction between a soil and the wet wipe when the cleansing composition also comprises a synergy enhancing agent. Sometimes, adding additional components to a cleansing composition for a wet wipe may negatively affect the sensory perception of the wet wipe to a user. For example, additional components may cause a cleansing composition to feel slimy or sticky. However, low concentrations of glucomannans may have little to no undesirable effect on the sensory perception of a wet wipe. As such, use of a cleansing composition comprising a glucomannan and a synergy enhancing agent in a wet wipe may provide good cleaning performance, while providing a wet wipe having a good sensory perception to consumers.

While glucomannans provide a cleansing composition having a good cleaning performance, glucomannans may be difficult to process. For example, glucomannans have a tendency to form a non-homogeneous, gel-like substance when combined with water. Surprisingly, it was found that combining a glucomannan with carrageenan improved the processability of a glucomannan. A mixture of carrageenan, glucomannan, and water may provide a homogeneous dispersion that may be subsequently combined with a synergy enhancing agent to form a cleansing composition.

In some exemplary configurations, a cleansing composition may comprise a glucomannan, carrageenan, and xanthan gum. In some exemplary configurations, the cleansing composition may be loaded onto a substrate to form a wet wipe.

While the present disclosure references the use of a wet wipe for cleaning skin, it is to be appreciated that the cleansing composition of the present disclosure may be used with various substrates, including tissues, paper towel, toilet paper, and the like. The substrates may be directly loaded with a cleansing composition or a cleansing composition may be applied to the substrate at the time of use in the form of a liquid or spray. In addition, the substrates of the present disclosure may be used to clean various other surfaces other than skin, including countertops, walls, floors, and the like.

Substrate

A cleansing composition of the present disclosure may be loaded onto a substrate to form a wet wipe. The substrate may be a nonwoven material. The nonwoven material may comprise one or more layers of such fibrous assemblies, wherein each layer may include continuous fibers, coextruded fibers, non-continuous fibers and combinations thereof.

The fibers of the substrate may be comprised of any natural, cellulosic, and/or wholly synthetic material. Examples of natural fibers may include cellulosic natural fibers, such as fibers from hardwood sources, softwood sources, or other non-wood plants. The natural fibers may comprise cellulose, starch and combinations thereof. Non-limiting examples of suitable cellulosic natural fibers include wood pulp, typical northern softwood Kraft, typical southern softwood Kraft, typical CTMP, typical deinked, corn pulp, acacia, eucalyptus, aspen, reed pulp, birch, maple, radiata pine and combinations thereof. Other sources of natural fibers from plants include albardine, esparto, wheat, rice, corn, sugar cane, papyrus, jute, reed, sabia, raphia, bamboo, sidal, kenaf, abaca, sunn, rayon (also known as viscose), lyocell, cotton, hemp, flax, ramie and combinations thereof. Yet other natural fibers may include fibers from other natural non-plant sources, such as, down, feathers, silk, cotton and combinations thereof. The natural fibers may be treated or otherwise modified mechanically or chemically to provide desired characteristics or may be in a form that is generally similar to the form in which they can be found in nature. Mechanical and/or chemical manipulation of natural fibers does not exclude them from what are considered natural fibers with respect to the development described herein.

The synthetic fibers can be any material, such as those selected from the group consisting of polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof. Further, the synthetic fibers can be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. Bicomponent fibers can be used as a component fiber of the structure, and/or they may be present to act as a binder for the other fibers present in the fibrous structure. Any or all of the synthetic fibers may be treated before, during, or after manufacture to change any desired properties of the fibers.

The substrate may comprise hydrophilic fibers, hydrophobic fibers, or a combination thereof.

The substrate may comprise various percentages of natural and/or synthetic fibers. For example, in some exemplary configurations, the substrate may comprise 100% synthetic fibers. In another exemplary configuration, the substrate may comprise natural and synthetic fibers. For example, the substrate may comprise from about 0% to about 90% natural fibers, with the balance comprising synthetic fibers. The substrate may be comprised of 10%, 20%, 30%, 40%, 50%, 60%, 70%, or 80% natural fibers.

In certain configurations, it may be desirable to have particular combinations of fibers to provide desired characteristics. For example, it may be desirable to have fibers of certain lengths, widths, coarseness or other characteristics combined in certain layers, or separate from each other. The fibers may be of virtually any size and may have an average length from about 1 mm to about 60 mm. Average fiber length refers to the length of the individual fibers if straightened out. The fibers may have an average fiber width of greater than about 5 micrometers. The fibers may have an average fiber width of from about 5 micrometers to about 50 micrometers. The fibers may have a coarseness of greater than about 5 mg/100 m. The fibers may have a coarseness of from about 5 mg/100 m to about 75 mg/100 m.

The fibers may be circular in cross-section, dog-bone shape, delta (i.e., triangular cross section), trilobal, ribbon, or other shapes typically produced as staple fibers. Likewise, the fibers can be conjugate fibers such as bicomponent fibers. The fibers may be crimped and may have a finish, such as a lubricant, applied.

The substrate materials may also be treated to improve the softness and texture thereof. The substrate may be subjected to various treatments, such as physical treatment, hydro-molding, hydro-embossing, and ring rolling, as described in U.S. Pat. No. 5,143,679; structural elongation, as described in U.S. Pat. No. 5,518,801; consolidation, as described in U.S. Pat. Nos. 5,914,084; 6,114,263; 6,129,801 and 6,383,431; stretch aperturing, as described in U.S. Pat. Nos. 5,628,097; 5,658,639; and 5,916,661; differential elongation, as described in U.S. Pat. No. 7,037,569, and other solid state formation technologies as described in U.S. Pat. No. 7,553,532 and U.S. Pat. No. 7,410,683; zone activation, and the like; chemical treatment, such as rendering part or all of the substrate hydrophobic, and/or hydrophilic, and the like; thermal treatment, such as thermal-embossing, softening of fibers by heating, thermal bonding and the like; and combinations thereof.

Without wishing to be bound by theory, it is believed that a textured substrate may further enable the ease of removal of soils by improving the ability to grip or otherwise lift the soils from the surface during cleansing. Any one of a number of texture elements may be useful in improving the ability to grip or otherwise lift the soil from the surface during cleansing such as continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, and the like, and combinations thereof. The texture elements may be hollow elements. The texture elements may be connected to each other. The texture elements may overlap each other.

The substrate may have a basis weight between about 15, 30, 40, or 45 grams/m$^2$ and about 65, 75, 85, 95, or 100 grams/m$^2$. A suitable substrate may be a carded nonwoven comprising a 40/60 blend of viscose fibers and polypropylene fibers having a basis weight of 58 grams/m$^2$ as available from Suominen of Tampere, Finland as FIBRELLA® 3160. FIBRELLA® 3160 is a 58 grams/m$^2$ nonwoven web comprising 60% by weight of 1.5 denier polypropylene fibers and 40% by weight of 1.5 denier viscose fibers. Another suitable material may be FIBRELLA® 3100 which is a 62 grams/m$^2$ nonwoven web comprising 50% by weight of 1.5 denier polypropylene fibers and 50% by weight of 1.5 denier viscose fibers. In both of these commercially available fibrous webs, the average fiber length is about 38 mm. Another suitable material for use as a substrate may be SAWATEX® 2642 as available from Sandler AG of Schwarzenbach/Salle, Germany. Yet another suitable material for use as a substrate may have a basis weight of from about 50 grams/m$^2$ to about 60 grams/m$^2$ and have a 20/80 blend of viscose fibers and polypropylene fibers. The substrate may also be a 60/40 blend of pulp and viscose fibers. Exemplary nonwoven substrates are described in U.S. Patent Publication 2012/066852 and U.S. Patent Publication U.S. 2011/244199.

In some configurations, the surface of the substrate may be essentially flat. In other configurations, the surface of the substrate may optionally contain raised and/or lowered portions. The raised and/or lowered portions can be in the form of logos, indicia, trademarks, geometric patterns, and/or images of the surfaces that the substrate is intended to clean (i.e., infant's body, face, etc.). The raised and/or lowered portions may be randomly arranged on the surface of the substrate or be in a repetitive pattern of some form.

In yet other configurations, the substrate may be biodegradable. For example, the substrate could be made from a biodegradable material such as a polyesteramide, or a high wet strength cellulose. In some exemplary configurations, the substrate may be dispersible.

Cleansing Composition

The cleansing composition of the present disclosure includes a glucomannan. In some exemplary configurations, the cleansing composition may include a glucomannan and a synergy enhancing agent. The cleansing composition also includes a carrier such as water. In addition, the cleansing composition may include various optional ingredients, such as surfactants, oil materials, film-formers, preservatives, pH buffers, rheology modifiers, and the like, such as described in U.S. Pat. Nos. 7,666,827; 7,005,557; 8,221,774; and U.S. Patent Application Publication No. 2011/0268777.

Glucomannan

As previously mentioned, the cleansing composition includes a glucomannan. Without being bound by theory, it is believed that a cleansing composition comprising a glucomannan improves the cleaning performance of a wet wipe. Using a cleansing composition comprising a glucomannan in a wet wipe may increase the adhesive interaction between the soil and the wet wipe above the adhesive interaction between the soil and the surface, thereby allowing the soil to detach from the surface upon wiping.

Various properties of glucomannans may be attributable to the increase in adhesive interaction between the wet wipe and the soil. For example, glucomannans are capable of absorbing up to 80-100 times the weight of the glucomannan of water. As discussed above, a wet wipe comprising high content of synthetic fibers may have a relatively high cleansing composition load dispersed throughout the wet wipe, as well as at the surface of the wet wipe. During the wiping process using such a wet wipe, the pressure applied to the wet wipe may interact with free water located at the interface of the wet wipe and the soil. Consequently, the free water may increase the lubricity of the wet wipe and reduce the adhesive interaction between the soil and the wet wipe. Without wishing to be bound by theory, it is believed that the water-absorbing capability of glucomannans may reduce the amount of free water dispersed throughout a wet wipe or otherwise enable this free water to be distributed in a way that prevents accumulation of free water at the soil-wipe interface. As a result, glucomannans may help to decrease the lubricity of the wet wipe, which may result in a greater adhesive interaction between the soil and the wet wipe, and hence better cleaning performance.

Glucomannans may also increase the peak complex viscosity of the cleansing composition. Cleansing compositions for wet wipes may be non-Newtonian, meaning that the viscosity of the cleansing composition changes with a change in strain, such as during the wiping process. Also, cleansing compositions for wet wipes may be shear-thinning, meaning that the viscosity of the cleansing composition decreases once a specific strain is reached. For example, the viscosity of the wipes cleansing composition may decrease when the wet wipe is wiped on a surface such as skin. A cleansing composition for wet wipes may also be viscoelastic, meaning that the cleansing composition includes viscous and elastic properties. Without wishing to be bound by theory, it is believed that increasing the viscoelasticity of the cleansing composition may increase the adhesive interaction between the soil and the wet wipe. The viscoelasticity of a cleansing composition may be evaluated using dynamic mechanical analysis, where an oscillatory stress is applied and the resulting strain is measured. The complex viscosity of a cleansing composition is the frequency-dependent viscosity determined under forced harmonic oscillation of shear stress. For shear-thinning compositions, the complex viscosity will be highest at low shear stress and will decrease as the composition is subjected to increasing shear stress and begins to shear thin. The highest complex viscosity obtained at low shear stresses may be referred to as peak complex viscosity or peak eta star. The higher the peak complex viscosity of the cleansing composition, the greater the viscoelasticity of the cleansing composition at low shear stresses.

Without wishing to be bound by theory, once the wet wipe is pulled away from the surface, the shear stress applied to the wet wipe decreases. As the shear stress decreases, the complex viscosity and associated viscoelasticity increases. This increased viscoelasticity helps to retain the soil on the surface of the wet wipe and to prevent it from falling back onto the surface being cleaned.

Glucomannans are also believed to have a good safety profile for use in a wet wipe as glucomannans are used in the food industry as thickening agents. The safety profile of a cleansing composition for a wet wipe is important because the wet wipes may be used on the skin of babies, including pre-term and full-term newborns.

Glucomannans, also referred to as polyglucomannans, are found in the corms of plants of the Araceae family. Glucomannan comprises roughly 40% of the roots of the konjac plant, also known as *Amorphophallus* konjac. It is also present in the wood of conifers and in the wood of dicotyledons. Common sources of glucomannan are the konjac plant. An exemplary form of konjac is manufactured by TIC Gums, Inc. of White Marsh, Md. under the designation TICAGEL® Konjac HV. Other exemplary forms of konjac is manufactured by FMC Biopolymer of Philadelphia, Pa. under the designations Nutricol XP3464 Nutricol ME8731, which includes a blend of konjac and carrageenan.

The cleansing composition may comprise from about 0.01% by weight to about 0.50% by weight of a glucomannan. The cleansing composition may comprise a single glucomannan, or the cleansing composition may comprise a combination of different glucomannans.

The peak complex viscosity of a cleansing composition comprising a glucomannan and a synergy enhancing agent for use in a wet wipe may be greater than about 0.8 Pascal·seconds (hereinafter "Pa·s"), greater than 2.5 Pa·s, or greater than about 3.0 Pa·s. The peak complex viscosity of a cleansing composition for use in a wet wipe may be in the range of about 1.0 Pa·s to about 5.0 Pa·s.

Synergy Enhancing Agent

As previously mentioned, the cleansing composition may comprise a glucomannan and one or more synergy enhancing agents. It has been found that a wet wipe having a cleansing composition comprising a synergy enhancing agent and a glucomannan has an improved cleaning performance compared to a wet wipe having a cleansing composition comprising a glucomannan without a synergy enhancing agent. As a result, lower concentrations of a glucomannan may be used in a cleansing composition comprising a synergy enhancing agent than may be used when the cleansing composition comprises a glucomannan without a synergy enhancing agent.

The cleansing composition may include one or more synergy enhancing agents. Non-limiting examples of synergy enhancing agents include xanthan gum, carrageenan, alginate, locust bean gum, starch, and gellan gum. Xanthan gum is available from Jungbunzlauer Austria.

The cleansing composition may comprise from about 0.1% by weight to about 0.5% by weight, or from about 0.12% by weight to about 0.18% by weight, of one or more synergy enhancing agents. The ratio of glucomannan to synergy enhancing agent present in the cleansing composition may be from about 1:1.5 to about 1:10.

An exemplary wet wipe may include a cleansing composition comprising glucomannan and xanthan gum. Another exemplary wet wipe may include a cleansing composition comprising glucomannan, carrageenan, and xanthan gum. In a cleansing composition comprising glucomannan, carrageenan, and xanthan gum, the ratio of xanthan gum to glucomannan to carrageenan may be from about 1:0.02:0.03 to about 1:0.33:0.5.

Figure 2:
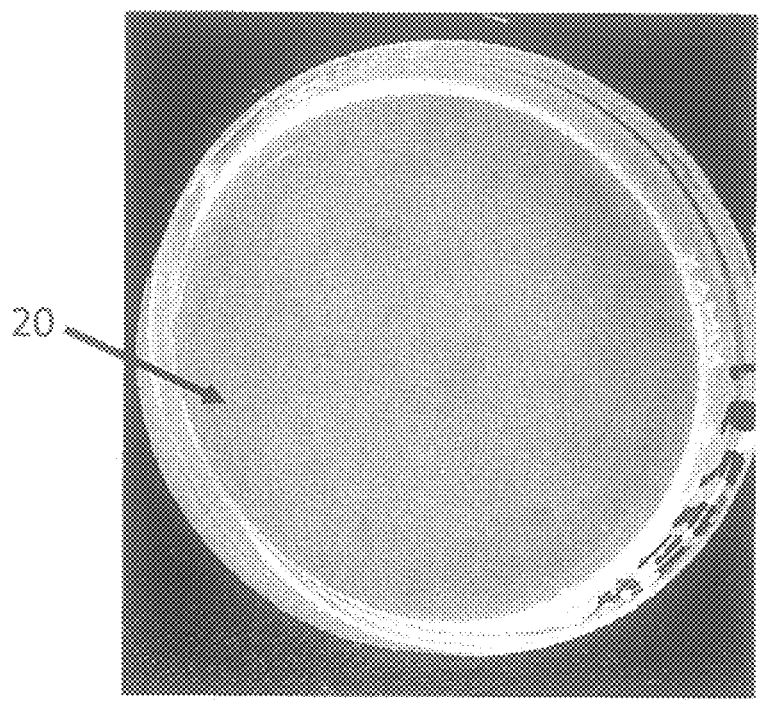
FIG. 2 is a black and white photograph of a beaker containing a homogeneous dispersion of a glucomannan and carrageenan in water.

However, when combined with water, glucomannans tend to form non-homogenous dispersions 10 having gel-like clumps 12 such as shown in FIG. 1. A non-homogeneous dispersion 10 such as shown in FIG. 1 may result in a non-homogeneous cleansing composition, which may negatively affect cleaning performance. Surprisingly, it was found that dispersing a combination of glucomannan and carrageenan in water results in a homogenous dispersion 20 that is free of gel-like clumps as shown in FIG. 2. The ratio of glucomannan to carrageenan may be in the range of about 0.02:0.03 to about 0.33:0.5. Further, after the glucomannan, carrageenan, and water form a homogeneous dispersion 20, a synergy enhancing agent such as xanthan gum may be added to form the cleansing composition.

The cleansing composition comprising a glucomannan and one or more synergy enhancing agents may be incorporated into a substrate at a load of about 200% to about 600% by weight of the substrate. A substrate comprising a relatively high amount of synthetic fibers may have a cleansing composition load of about 400% to about 600% by weight of the substrate.

Optional Cleansing Composition Ingredients

Additional ingredients may be added to the cleansing composition. The cleansing composition may generally comprise any of the following ingredients: oil materials, surfactants, rheology modifiers, preservatives, or a combination of preservative compounds acting together as a preservative system or other adjunct ingredients. It is to be noted that some ingredient compounds can have a multiple function and that all compounds are not necessarily present in the cleansing composition. The cleansing composition may be an aqueous-based solution. The pH of the composition may be from about pH 3, 4, or 5 to about pH 7, 7.5, or 8. In some exemplary configurations, the pH may be from about 3.5 to about 4.

Oil Material

The cleansing composition may include an oil material. Oil materials may (1) hydrate the residues (for example, fecal residues or dried urine residues or menses), thus enhancing their removal from the skin, (2) hydrate the skin, thus reducing its dryness and irritation while improving its flexibility under the wiping movement, (3) reduce the adhesive interaction between the soil and the surface, and (4) protect the skin from later irritation (for example, caused by the friction of an absorbent article) as the oil material is deposited onto the skin and remains at its surface as a thin protective layer.

Oil materials may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The oil materials may be either saturated or unsaturated, have an aliphatic character and be straight or branched chained or contain alicyclic or aromatic rings. In some exemplary configurations, the cleansing composition may comprise a mixture of caprylic/capric triglycerides in combination with Bis-PEG/PPG-16/16 PEG/PPG-16/16 dimethicone known as ABIL® CARE 85, available from Degussa Care Specialties of Hopewell, Va.

Oil materials, when present in the cleansing composition, may be present at an amount of less than about 0.5%, 0.4%, 0.3%, 0.2%, or 0.1% by weight of the cleansing composition. It is believed that minimal amounts of oil materials are desirable for adequate cleaning performance of the cleansing composition. Cleansing compositions comprising oil materials have a tendency to form a greasy or oily layer on the surface being wiped, which may increase the lubricity of the wet wipe against the surface and reduce the adhesive interaction between the wet wipe and the surface. Also, a greasy or oily layer on a surface such as skin may not be preferred by consumers. Therefore, it may be desirable for the cleansing composition to comprise enough of an oil material to provide benefits to the skin without compromising the cleaning performance.

Surfactant

The cleansing composition may include one or more surfactants. The surfactant can be an individual surfactant or a mixture of surfactants. The surfactant may be a polymeric surfactant or a non-polymeric one. The primary purpose of the surfactant is to aid in dissolution and removal of the soils from the surface being cleansed. The surfactant or combinations of surfactants may be mild, which means that the surfactants provide sufficient cleaning or detersive benefits but do not overly dry or otherwise harm or damage the skin. The surfactant, when present in the cleansing composition, may be present in an amount ranging from about 0.5%, 1%, or 4% by weight to about 0.001%, 0.01% or 0.02% by weight of the cleansing composition.

A wide variety of surfactants are useful herein and include those selected from the group consisting of anionic surfactants, nonionic surfactants, cationic surfactants, amphoteric surfactants, zwitterionic surfactants, and mixtures thereof.

A wide variety of anionic surfactants are useful herein. Non-limiting examples of anionic surfactants include those selected from the group consisting of carboxylates, sarcosinates, sulfates, sulfonates, isethionates, taurates, phosphates, lactylates, glutamates, and mixtures thereof.

Nonionic surfactants useful herein include, but are not limited to, those selected from the group consisting of alkyl glucosides, alkyl polyglucosides, polyhydroxy fatty acid amides, alkoxylated fatty acid esters, alkoxylated fatty alcohol ethers, sucrose esters, and mixtures thereof.

Amphoteric surfactants suitable for use in the present compositions include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Useful amphoteric surfactants include the group consisting of cocoamphoacetate, cocoamphodiacetate, lauroamphoacetate, lauroamphodiacetate, and mixtures thereof.

Zwitterionic surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Useful zwitterionic surfactants include betaines, amphoacetates and sulfobetaines, e.g., cocoamidopropylbetaine, sodium laurylamphoacetate and cocoamidopropylhydroxysultaine.

Rheoloey Modifier

The cleaning composition may comprise one or more rheology modifiers. A rheology modifier may (1) help to stabilize the cleansing composition on a substrate, (2) enhance the transfer of the cleansing composition to the skin, and (3) enhance the uniformity of the layer of the cleansing composition on the skin. For example, rheology modifiers may help to preserve a homogeneous distribution of the cleansing composition within a stack of the substrates. Any composition that is in fluid form may have a tendency to migrate to the lower part of the wipes stack during prolonged storage. This effect may create an upper part of the stack of substrates having less cleansing composition than the bottom part of the stack.

Non-limiting examples of rheology modifiers include, but are not limited to, rheology modifiers comprising:

polysaccharide units, e.g. cellulose, xanthan gum, diutan gum, carrageenan, gellan gum, welan gum, pectin, sclerotium gum, starch, galactoarabinan, alginate, and modified-forms thereof;

homopolymers of acrylic acid;

acrylic acid cross-linked with a polyfunctional compound, e.g. carbomer and acrylate crosspolymer;

copolymers of acrylic acid, acrylate esters, maleic acid and the like, generally known as the alkali swellable emulsions (ASE) group;

hydrophobically-modified copolymers of acrylic acid, acrylate esters, maleic acid and the like, generally known as the hydrophobically-modified alkali swellable emulsions (HASE) group;

polyethylene glycol units of varying length connected by urethane linkages and terminated with hydrophobic end groups, generally known as the hydrophobically-modified ethoxylated urethane resins (HEUR) group;

organoclays;

silicas; and combinations thereof.

Rheology modifiers, when present in the cleansing composition, may be present in the range of about 0.01%, 0.015%, or 0.02% by weight to about 1% by weight of the cleansing composition.

Preservative

Controlling microbiological growth may be beneficial in water based products such as cleansing compositions intended for use in wet wipes. The cleansing composition may comprise a preservative or a combination of preservatives acting together as a preservative system. Preservatives and preservative systems are used interchangeably in the present disclosure to indicate one unique or a combination of preservative compounds. A preservative may be understood to be a chemical or natural compound or a combination of compounds reducing the growth of microorganisms, thus enabling a longer shelf life for a package of substrates (opened or not opened) as well as creating an environment with reduced growth of microorganisms when transferred to the skin during the wiping process.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Materials useful as preservatives include methylol compounds, iodopropynyl compounds, simple aromatic alcohols, paraben compounds, benzyl alcohol, benzoic acid, benzoates, sorbic acid, sorbates, phenoxyethanol, ethxylhexyglycerin, chelators such as ethylenediamine tetraacetic acid, and combinations thereof. Suitable preservative systems are described in U.S. Patent Publication No. 2005/0008680 and U.S. Patent Publication No. 2005/0008681.

Low pH buffering systems, such as a citrate-citric acid buffering system at a pH of less than about 5, may also be employed as part of the preservative system.

In some exemplary configurations, the preservative system may comprise simple aromatic alcohols (e.g. benzyl alcohol). Materials of this type may have effective antibacterial activity. Benzyl alcohol is available from Symrise, Inc. of Teterboro, N.J. In other exemplary configurations, the preservative system may comprise a mixture of benzyl alcohol, sodium benzoate, phenoxyethanol, ethylhexylglycerin, ethylenediamine tetraacetic acid, citric acid, and sodium citrate dehydrate wherein the pH of the cleansing composition is less than about 4. The total concentration of benzyl alcohol may be lower than about 0.4% by weight of the cleansing composition. The total concentration of sodium benzoate may be lower than about 0.3% by weight of the cleansing composition. The combination of phenoxyethanol and ethylhexylglycerin, which are available as EUXYL® PE 9010 from Schulke & Mayr GmbH of Germany, may be lower than about 0.4%.

In some exemplary configurations, acidic compounds used in sufficient amount to reduce the pH of the cleansing composition (e.g. pH of less than about 5) may be useful as the preservative, or as a potentiator for other preservative ingredients.

In other exemplary configurations, chelators, such as ethylenediamine tetraacetic acid and its salts, may also be used in preservative systems as a potentiator for other preservative ingredients.

Adjunct Ingredients

The cleansing composition may optionally include other adjunct ingredients. Possible adjunct ingredients may be selected from a wide range of additional ingredients such as perfumes and fragrances, texturizers, colorants, soothing agents and medically active ingredients, such as healing actives and skin protectants.

Method of Making a Cleansing Composition:

Cleansing compositions such as Examples 1 and 2 shown below may be prepared at a temperature in the range of 20-25° C. according to the following method.

1. Disperse TICAGEL® Konjac HV in water and mix with an ULTRA-TURRAX® mixer (for example, model T-50 with a S 50 N-80 SMK Jet mixer head, available from IKA Works of Wilmington, N.C.) at 4000-5000 rpm for 15 minutes.
2. Add disodium EDTA, sodium benzoate, and trisodium citrate to the dispersion of Step 1 and mix with the ULTRA-TURRAX® mixer at 5000-6000 rpm for 3 minutes.
3. Add xanthan gum and Ritaloe 200M to the dispersion of Step 2 and mix with the ULTRA-TURRAX® mixer at 5000-6000 rpm for 15 minutes.
4. Add EMULSOGEN® HCW 049 to the dispersion of Step 3 and mix with the ULTRA-TURRAX® mixer at 5000-6000 rpm for 3 minutes.
5. Add ABIL® Care 85 to the dispersion of Step 4 and mix with the ULTRA-TURRAX® mixer at 5000-6000 rpm for 3 minutes.
6. Add EUXYL® PE 9010 to the dispersion of Step 5 and mix with the ULTRA-TURRAX® mixer at 5000-6000 rpm for 3 minutes.
7. Add benzyl alcohol, phytoconcentrol 2066530 and citric acid to the dispersion of Step 6 and mix with the ULTRA-TURRAX® mixer at 5000-6000 rpm for 10 minutes Cleansing compositions such Example 3 shown below may be prepared at a temperature in the range of 20-25° C. according to the following method.

1. Disperse FMC NUTRICOL® ME 8731 in water and mix with the ULTRA-TURRAX® mixer at 4000-5000 rpm for 15 minutes.
2. Add disodium EDTA, sodium benzoate, and trisodium citrate to the dispersion of Step 1 and mix with the ULTRA-TURRAX® mixer at 5000-6000 rpm for 3 minutes.
3. Add xanthan gum to the dispersion of Step 2 and mix with the ULTRA-TURRAX® mixer at 5000-6000 rpm for 15 minutes.
4. Add EMULSOGEN® HCW 049 to the dispersion of Step 3 and mix with ULTRA-TURRAX® mixer at 5000-6000 rpm for 3 minutes.
5. Add ABIL® Care 85 to the dispersion of Step 4 and mix with the ULTRA-TURRAX® mixer at 5000-6000 rpm for 3 minutes.
6. Add EUXYL® PE 9010 to the dispersion of Step 5 and mix with the ULTRA-TURRAX® mixer at 5000-6000 rpm for 3 minutes.
7. Add benzyl alcohol and citric acid to the dispersion of Step 6 and mix with the ULTRA-TURRAX® mixer at 5000-6000 rpm for 10 minutes.

EXAMPLES

Example 1 is an illustrative, non-limiting formula for a cleansing composition comprising konjac and xanthan gum.

Example 1

| Ingredient Name | Weight % |
| --- | --- |
| Water | Q.S. |
| Konjac* | 0.025 |
| Disodium EDTA | 0.100 |
| Sodium Benzoate | 0.120 |
| Trisodium Citrate | 0.330 |
| Xanthan Gum | 0.180 |
| Aloe Barbadensis Leaf Extract† | 0.003 |
| Peg-40 Hydrogenated Castor Oil▫ | 0.440 |
| BIS-PEG/PPG-16/16 PEG/PPG-16/16 Dimethicone Caprylic Capric Triglyceride△ | 0.100 |
| Phenoxyethanol Ethylhexylglycerine° | 0.300 |
| Benzyl Alcohol | 0.300 |
| Bisabolol, Caprylic Capric Triglycerides, Chamomilla, Recutita Matricaria Flower Extract◊ | 0.003 |
| Citric Acid | 0.530 |
| Total | 100 |

*TICAGEL ® Konjac HV, available from TIC Gums, Inc. of White Marsh, MD
†Ritaloe 200M, available from R.I.T.A. Corporation of Crystal Lake, Illinois
▫EMULSOGEN ® HCW 049, available from Clariant Corporation of Charlotte, NC
△ABIL ® Care 85, available from Evonik Industries of Germany
°EUXYL ® PE 9010, available from Schulke & Mayr GmbH of Germany
◊Phytoconcentrol 2066530, available from Symrise AG of Holzminden, Germany Example 2 is an illustrative, non-limiting formula for a cleansing composition comprising konjac and xanthan gum.

Example 2

| Ingredient Name | Weight % |
| --- | --- |
| Water | Q.S. |
| Konjac* | 0.075 |
| Disodium EDTA | 0.100 |
| Sodium Benzoate | 0.240 |
| Trisodium Citrate | 0.260 |
| Xanthan Gum | 0.180 |
| Aloe Barbadensis Leaf Extract† | 0.003 |
| Peg-40 Hydrogenated Castor Oil▫ | 0.440 |
| BIS-PEG/PPG-16/16 PEG/PPG-16/16 Dimethicone Caprylic Capric Triglyceride△ | 0.100 |
| Phenoxyethanol Ethylhexylglycerine° | 0.300 |
| Benzyl Alcohol | 0.300 |
| Bisabolol, Caprylic Capric Triglycerides, Chamomilla, Recutita Matricaria Flower Extract◊ | 0.003 |
| Citric Acid | 0.550 |
| Total | 100 |

*TICAGEL ® Konjac HV
†Ritaloe 200M
▫EMULSOGEN ® HCW 049
△ABIL ® Care 85
°EUXYL ® PE 9010
◊Phytoconcentrol 2066530

Example 3 is an illustrative, non-limiting formula for a cleansing composition comprising konjac, carrageenan, and xanthan gum.

Example 3

| Ingredient Name | Weight % |
| --- | --- |
| Water | Q.S. |
| FMC Nutricol ME 8731* | 0.050 |
| Disodium EDTA | 0.100 |
| Sodium Benzoate | 0.120 |
| Trisodium Citrate | 0.330 |
| Xanthan Gum | 0.180 |
| Peg-40 Hydrogenated Castor Oil▫ | 0.440 |
| BIS-PEG/PPG-16/16 PEG/PPG-16/16 Dimethicone Caprylic Capric Triglyceride△ | 0.100 |
| Phenoxyethanol Ethylhexylglycerine° | 0.300 |
| Benzyl Alcohol | 0.300 |
| Citric Acid | 0.530 |
| Total | 100 |

*blend of konjac and carrageenan, manufactured by FMC BioPolymer of Rockland, ME
▫EMULSOGEN ® HCW 049
△ABIL ® Care 85
°EUXYL ® PE 9010

Peak Complex Viscosity Method

This method is suitable for determination of peak complex viscosity of a lotion composition. A Haake Rheostress 600 rotational rheometer available from Thermo Fisher Scientific of Waltham, Mass. or equivalent instrument is used. A 60 mm diameter parallel plate fixture is used and the temperature of the specimen is controlled to 25±1° C. during the viscosity measurement by means of a suitable circulating water bath.

The instrument is programmed to run in Amplitude Sweep mode at a frequency of 0.16 Hz starting at a shear stress Tau=0.05 Pa and ending at Tau=25.6 Pa with a maximum measurement time of 300 seconds. The amplitude is increased in 10 steps on a linear scale using the following Tau values:

| Step | Tau [Pa] |
| --- | --- |
| 1 | 0.05 |
| 2 | 0.10 |
| 3 | 0.20 |
| 4 | 0.40 |
| 5 | 0.80 |
| 6 | 1.60 |
| 7 | 3.20 |
| 8 | 6.40 |
| 9 | 12.80 |
| 10 | 25.60 |

The instrument is calibrated for inertia and zero gap according to the procedures specified by the instrument manufacturer. The plates are separated and cleaned with a suitable solvent and allowed to dry. A sufficient quantity of the lotion composition is deposited onto the center of the base plate using a suitable pipette or equivalent to ensure that the lotion composition will completely fill the gap when the plates are brought together. Typically this is approximately 2.5 ml of the lotion composition. The gap is then closed to 0.800 mm and the sample is trimmed by running a rubber policeman or equivalent around the periphery of the plates to remove any excess lotion. The test is then initiated and the relevant data (complex viscosity Eta* as a function of shear stress Tau) are acquired.

The Peak Complex Viscosity is the highest recorded value for Eta*. This value can be obtained directly from the raw data.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleansing composition comprising a glucomannan, xanthan gum, and carrageenan, wherein the ratio of xanthan gum to glucomannan to carrageenan is from about 1:0.02:0.03 to about 1:0.33:0.5.

2. The cleansing composition of claim 1, wherein the glucomannan comprises *Amorphophallus* konjac root powder.

3. The cleansing composition of claim 1, wherein the cleansing composition comprises less than about 0.25% by weight of the glucomannan.

4. The cleansing composition of claim 1, wherein the cleansing composition has a peak complex viscosity of between about 0.8 Pa·s to about 7.0 Pa·s.

5. A wet wipe comprising a substrate and the cleansing composition of claim 1.

6. The wet wipe of claim 5, wherein the substrate comprises a nonwoven.

7. The wet wipe of claim 5, wherein the wet wipe comprises from about 200% to about 600% by weight of the substrate of cleansing composition.

8. A method of preparing a cleansing composition, the method comprising the steps of:
dispersing glucomannan and carrageenan in water in a pre-mixing step;
adding xanthan gum to the dispersion of glucomannan, carrageenan, and water; and
mixing the xanthan gum in the dispersion of glucomannan, carrageenan, and water to form a cleansing composition wherein the ratio of xanthan gum to glucomannan to carrageenan is from about 1:0.02:0.03 to about 1:0.33:0.5.

9. The method of claim 8, wherein the cleansing composition has a peak complex viscosity of between about 0.8 Pa·s to about 7.0 Pa·s.

10. The method of claim 8 further comprising the step of loading the cleansing composition onto a substrate to form a wet wipe.

11. The method of claim 10, wherein the wet wipe comprises from about 200% to about 600% by weight of the substrate of cleansing composition.

* * * * *